(12) United States Patent
Hijikuro et al.

(10) Patent No.: US 9,211,067 B2
(45) Date of Patent: Dec. 15, 2015

(54) DETECTION DEVICE, DETECTING METHOD, CONTROL PROGRAM AND RECORDING MEDIUM

(75) Inventors: Megumi Hijikuro, Osaka (JP); Mikihiro Yamanaka, Osaka (JP); Keita Hara, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 336 days.

(21) Appl. No.: 13/878,542

(22) PCT Filed: Oct. 5, 2011

(86) PCT No.: PCT/JP2011/073011
§ 371 (c)(1),
(2), (4) Date: Apr. 9, 2013

(87) PCT Pub. No.: WO2012/050030
PCT Pub. Date: Apr. 19, 2012

(65) Prior Publication Data
US 2013/0197372 A1    Aug. 1, 2013

(30) Foreign Application Priority Data

Oct. 12, 2010    (JP) ................... 2010-229474

(51) Int. Cl.
*A61B 6/00*    (2006.01)
*A61B 5/00*    (2006.01)
*G01N 21/64*    (2006.01)

(52) U.S. Cl.
CPC ............ *A61B 5/0071* (2013.01); *G01N 21/645* (2013.01); *G01N 21/6486* (2013.01)

(58) Field of Classification Search
CPC .................................................. A61B 5/0071
USPC ......................... 600/407, 473–480
See application file for complete search history.

(56) References Cited

U.S. PATENT DOCUMENTS

| | | | | |
|---|---|---|---|---|
| 5,105,305 | A | * | 4/1992 | Betzig et al. ................ 359/368 |
| 5,655,530 | A | | 8/1997 | Messerschmidt |
| 5,823,951 | A | | 10/1998 | Messerschmidt |
| 5,874,726 | A | * | 2/1999 | Haydon .................. 250/201.1 |
| 6,123,719 | A | * | 9/2000 | Masychev .................. 600/407 |
| 6,152,876 | A | | 11/2000 | Robinson et al. |
| 6,212,424 | B1 | | 4/2001 | Robinson |
| 6,240,306 | B1 | | 5/2001 | Rohrscheib et al. |

(Continued)

FOREIGN PATENT DOCUMENTS

| | | |
|---|---|---|
| JP | 3-8749 U | 1/1991 |
| JP | 7-286958 A | 10/1995 |

(Continued)

*Primary Examiner* — James Kish
(74) *Attorney, Agent, or Firm* — Birch, Stewart, Kolasch & Birch, LLP

(57) ABSTRACT

A detection device (1) includes a light receiving unit (13a) which receives fluorescence; a light receiving intensity calculation unit (32) which calculates light receiving intensity of fluorescence which is received by the light receiving unit (13a) while changing a relative position (L) between the light receiving unit (13a) and a test subject (100); and a specifying unit (33) which specifies an optimal position of the relative position (L) where the light receiving intensity which is calculated by the light receiving intensity calculation unit (32) becomes a maximum, and in which fluorescence is detected using the optimal position which is specified by the specifying unit (33).

8 Claims, 13 Drawing Sheets

(56) References Cited

U.S. PATENT DOCUMENTS

| | | |
|---|---|---|
| 6,622,032 B1 | 9/2003 | Robinson et al. |
| 6,865,408 B1 | 3/2005 | Abbink et al. |
| 2001/0018560 A1 | 8/2001 | Robinson |
| 2002/0035341 A1 | 3/2002 | Rohrscheib et al. |
| 2002/0117632 A1* | 8/2002 | Hakamata et al. ......... 250/458.1 |
| 2003/0007147 A1 | 1/2003 | Johnson |
| 2003/0023152 A1 | 1/2003 | Abbink et al. |
| 2003/0023170 A1 | 1/2003 | Gardner et al. |
| 2003/0191378 A1 | 10/2003 | Davis, III et al. |
| 2004/0051051 A1 | 3/2004 | Kato et al. |
| 2004/0082070 A1 | 4/2004 | Jones et al. |
| 2004/0167382 A1 | 8/2004 | Gardner et al. |
| 2005/0090750 A1 | 4/2005 | Ediger et al. |
| 2005/0148834 A1 | 7/2005 | Hull et al. |
| 2005/0203343 A1* | 9/2005 | Kang et al. .................... 600/160 |
| 2005/0261560 A1 | 11/2005 | Ridder et al. |
| 2006/0167349 A1 | 7/2006 | Gardner et al. |
| 2006/0173256 A1 | 8/2006 | Ridder et al. |
| 2006/0178570 A1 | 8/2006 | Robinson et al. |
| 2006/0211928 A1 | 9/2006 | Hull et al. |
| 2007/0073118 A1 | 3/2007 | Ridder et al. |
| 2007/0088205 A1 | 4/2007 | Hull et al. |
| 2007/0142720 A1 | 6/2007 | Ridder et al. |
| 2007/0197880 A1 | 8/2007 | Maynard et al. |
| 2007/0265532 A1 | 11/2007 | Maynard et al. |
| 2007/0276199 A1 | 11/2007 | Ediger et al. |
| 2008/0097174 A1 | 4/2008 | Maynard et al. |
| 2008/0103373 A1 | 5/2008 | Matter et al. |
| 2008/0103396 A1 | 5/2008 | Johnson et al. |
| 2008/0208018 A1 | 8/2008 | Ridder et al. |
| 2008/0319286 A1 | 12/2008 | Ridder et al. |
| 2009/0003764 A1 | 1/2009 | Ridder et al. |
| 2009/0018415 A1 | 1/2009 | Robinson et al. |
| 2009/0234204 A1 | 9/2009 | Ridder et al. |
| 2010/0010325 A1 | 1/2010 | Ridder et al. |
| 2011/0178420 A1 | 7/2011 | Ridder et al. |
| 2011/0184260 A1 | 7/2011 | Robinson et al. |
| 2011/0282167 A1 | 11/2011 | Ridder et al. |
| 2012/0065484 A1 | 3/2012 | Hull et al. |
| 2012/0078075 A1 | 3/2012 | Maynard et al. |
| 2012/0078473 A1 | 3/2012 | Ridder et al. |
| 2012/0179010 A1 | 7/2012 | Maynard et al. |
| 2012/0197096 A1 | 8/2012 | Ridder et al. |
| 2012/0283531 A1 | 11/2012 | Maynard et al. |

FOREIGN PATENT DOCUMENTS

| | | |
|---|---|---|
| JP | 2004-75268 A | 3/2004 |
| JP | 2004-279258 A | 10/2004 |
| JP | 2004-309428 A | 11/2004 |
| JP | 2007-510159 A | 4/2007 |
| JP | 2007-198883 A | 8/2007 |
| JP | 2008-510965 A | 4/2008 |
| JP | 2009-14379 A | 1/2009 |
| WO | WO 02/48693 A1 | 6/2002 |
| WO | WO 2006/023725 A2 | 3/2006 |

* cited by examiner

F I G. 1
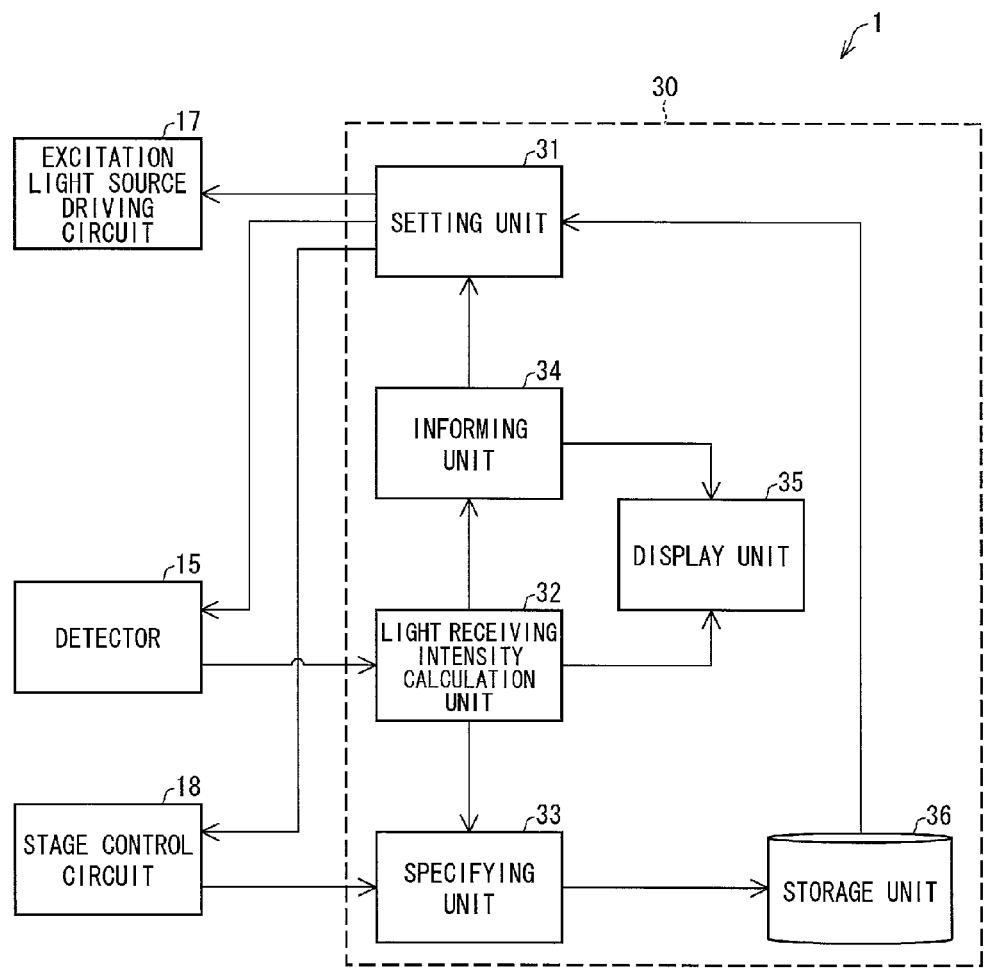

F I G. 3
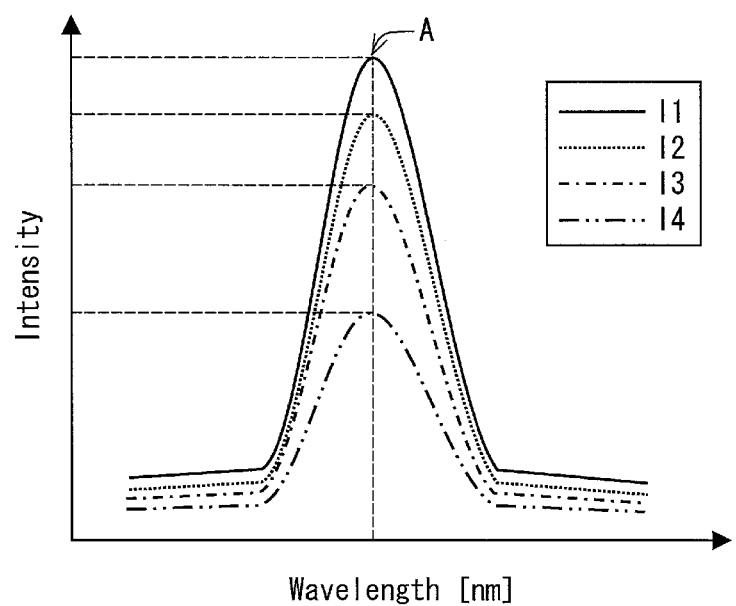

F I G. 9
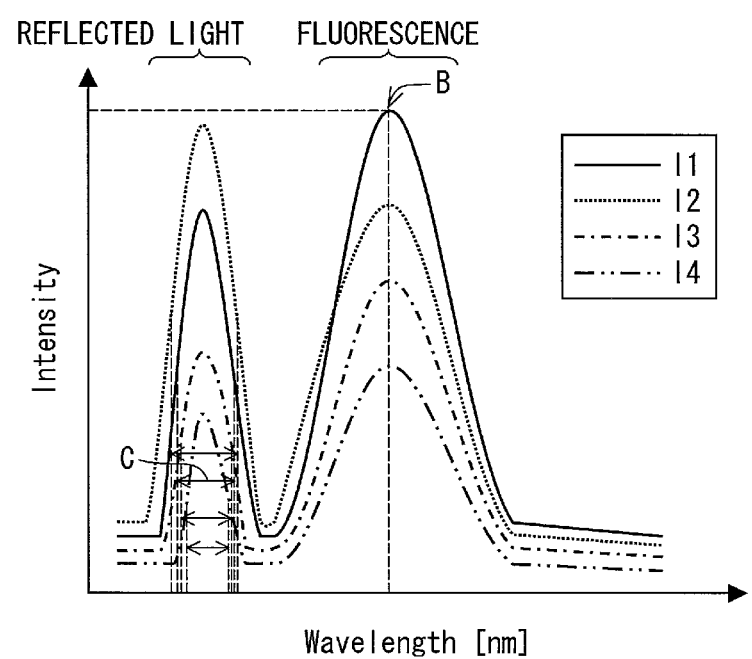

DETECTION DEVICE, DETECTING METHOD, CONTROL PROGRAM AND RECORDING MEDIUM

TECHNICAL FIELD

The present invention relates to a detection device which detects fluorescence which is radiated from a test subject due to irradiation of excitation light, a detecting method, a control program, and a recording medium.

BACKGROUND ART

In recent years, with westernization of diets, patients of lifestyle-related diseases are increasing, and resulting in serious medical and social problems. At present, in Japan, the number of diabetic patients is 8,000,000, and it is also said that the number of diabetic patients plus pre-diabetic patients reaches 20,000,000. The three main complications of diabetes are retinopathy, nephropathy, and neuropathy. Diabetes is also a cause for arteriosclerosis. Furthermore, diabetes may cause heart diseases and brain diseases.

A person develops diabetes in such a manner that improper diets and life styles, secretion from fat cells due to fatness, or oxidative stress decreases the function of pancreas, causing shortage of insulin that controls a blood glucose level or reducing the effect of insulin. Diabetes has symptoms such as frequent urination and increased amount of urination, and increased thirst. However, such symptoms may not enable patients to realize that they have developed diabetes, and most patients know their illness when they are subjected to examination in hospitals, etc. This explains why there are so many "silent" diabetic patients.

At the stage where abnormal symptoms resulting from the complications of diabetes are found in hospitals, etc., conditions of the disease have advanced too far, making it difficult to completely cure the disease. In particular, many of the complications of diabetes are difficult to cure, and therefore prevention of diabetes is considered as important as like many life-style related diseases. For the prevention, early identification and early determination of therapeutic effect are essential, and there are many inspections for diabetes for this purpose.

When a person undergoes oxidative stress in a situation where blood contains abnormal amounts of carbohydrates and lipids therein, the oxidative stress causes reactions of the carbohydrates and the lipids with protein so that AGEs (Advanced Glycation Endproducts) are produced. AGEs are end products produced via non-enzymatic glycosylation reaction of protein (Maillard reaction). AGEs exhibit yellowish brown color, emit fluorescence, and form crosslinks by bonding to nearby proteins.

AGEs are considered to be deposited on and infused into blood vessel walls or to interact with macrophage which is a part of an immune system, to thereby release cytokine that is one type of protein and to cause inflammation, resulting in arteriosclerosis.

In the case of diabetes, as the blood glucose level increases, the amount of AGEs increases. Accordingly, by monitoring AGEs, it is possible to identify diabetes at an early stage or to comprehend the progress of diabetes. One example of a method for screening diabetes mellitus by monitoring AGEs is reported in PTL 1.

With the reported method, AGEs are monitored by irradiating the skin of a forearm with excitation light, detecting a fluorescence spectrum from the AGEs bound to skin collagen, and comparing the detected fluorescence spectrum with a predetermined model. Thus, AGEs data is obtained in a non-invasive manner.

CITATION LIST

Patent Literature

PTL 1: Japanese Unexamined Patent Application Publication "Translation of PCT Application No. 2007-510159 (published on Apr. 19, 2007)"

SUMMARY OF INVENTION

Technical Problem

Meanwhile, it is known that a detection strength of fluorescence heavily depends on a relative position (for example, distance) between a living body and a detection unit which detects radiated fluorescence when irradiating the living body such as the skin of a forearm, as described above, with excitation light, and detecting the fluorescence which is radiated from the living body.

However, in the method which is disclosed in PTL 1, a stand for a forearm which is a fixture which maintains a fiber bundle formed by a light source fiber, and a detector fiber in a state of being in contact with the skin of a test subject. A distance between the fiber bundle and a portion to be detected which is a palm side forearm is determined using the stand.

For this reason, when the portion to be detected is deviated due to a movement of a test subject, the distance between the fiber bundle, in particular, the detector fiber in the fibers and the portion to be detected is easily changed. In such a case, there has been a problem in that it is not possible to accurately detect the fluorescence which is radiated from the portion to be detected.

In addition, usually, a size or a weight of a forearm varies in each test subject. For this reason, there has been a problem in that a position of the portion to be detected is largely deviated from the original position depending on a test subject, and as a result, it is not possible to accurately detect the fluorescence which is radiated from the portion, when a plurality of test subjects are detected using the same fixture.

In addition, when detections in various portions of a test subject are performed, it is necessary to prepare an individual fixture with a shape which is suitable for positioning each portion. Accordingly, there also has been a problem in that the detection device becomes expensive.

The present invention has been made in consideration of the above described problems, and an object thereof is to provide a detection device which is able to detect fluorescence, which is radiated from a test subject such as a living body, with high precision, and inexpensively, a detecting method, a control program, and a recording medium thereof.

Solution to Problem

A detection device according to the present invention is a detection device which irradiates a test subject with excitation light, and detects fluorescence which is radiated from the test subject in order to solve the above described problems. The detection device includes a light receiving unit which receives the fluorescence; means for calculating a light receiving intensity of fluorescence which is received by the light receiving unit while changing a relative position between the light receiving unit and the test subject; and means for specifying an optimal position of the relative position where the light receiving intensity which is calculated by the means for calculating the light receiving intensity becomes a maximum, in which the fluorescence is detected using the optimal position which is specified by the means for specifying.

A detecting method according to the present invention is a detecting method in which excitation light is radiated to the test subject, and fluorescence which is radiated from the test subject is detected, and the method includes a step of calculating a light receiving intensity of fluorescence which is received by the light receiving unit while changing a relative position between the light receiving unit which receives the fluorescence and the test subject; a step of specifying an optimal position of the relative position where the light receiving intensity of fluorescence which is calculated in the step of calculating the light receiving intensity becomes a maximum; and a step of detecting the fluorescence using the optimal position which is specified in the step of specifying.

It is known that a light receiving intensity of fluorescence which is radiated from a test subject depends on a relative position between a light receiving unit which receives the fluorescence and a test subject. That is, when a relative position between both is changed, a light receiving intensity of fluorescence which is received is also changed along with the change.

Here, the "light receiving intensity" is a peak value of an intensity of fluorescence which is received by a light receiving unit, and the peak value is changed according to a change in the relative position between a light receiving unit and a test subject.

According to above configuration, fluorescence is received while changing a relative position between a light receiving unit and a test subject, and an optimal position of a relative position where a light receiving intensity of the fluorescence becomes a maximum is specified. When using the specified optimal position, it is possible to maximize the light receiving intensity of fluorescence using a light receiving unit.

In this manner, it is possible to perform detecting of fluorescence at a position where the light receiving intensity becomes the maximum, and to detect the fluorescence which is radiated from a test subject with high precision.

In addition, when specifying the optimal position, it is enough to receive fluorescence while changing a relative position between a light receiving unit and a test subject. It is not necessary to prepare for a large or an expensive additional mechanism separately, in order to specify the optimal position.

For this reason, it is possible to maximize the intensity of light received by a light receiving unit when detecting fluorescence which is radiated from a test subject, without using a special additional mechanism.

As a result, it is possible to detect fluorescence with high precision, and inexpensively.

Advantageous Effects of Invention

A detection device according to the present invention is a detection device which irradiates a test subject with excitation light, and detects fluorescence which is radiated from the test subject in order to solve the above described problems. The detection device includes a light receiving unit which receives the fluorescence; light receiving intensity calculation means which calculates a light receiving intensity of fluorescence which is received by the light receiving unit while changing a relative position between the light receiving unit and the test subject; and specification means which specifies an optimal position of the relative position where the light receiving intensity which is calculated by the light receiving intensity calculation means becomes a maximum, and in which the fluorescence is detected using the optimal position which is specified by the specification means.

A detecting method according to the present invention is a detecting method in which excitation light is radiated to the test subject and fluorescence which is radiated from the test subject is detected in order to solve the above described problems, and the method includes a step of calculating a light receiving intensity of fluorescence which is received by the light receiving unit while changing a relative position between the light receiving unit which receives the fluorescence and the test subject; a step of specifying an optimal position of the relative position where the light receiving intensity of the fluorescence which is calculated in the step of calculating the light receiving intensity becomes a maximum; and a step of detecting the fluorescence using the optimal position which is specified in the step of specifying.

In addition, it is possible to obtain effects of realizing a detection device in which fluorescence which is radiated from a test subject such as a living body can be detected with high precision, and inexpensively, and a detecting method thereof.

BRIEF DESCRIPTION OF DRAWINGS

FIG. 1 is a block diagram which illustrates a configuration of a detection device according to an embodiment of the present invention.

FIG. 3 is a graph which illustrates a calculation result of light receiving intensity of fluorescence.

FIG. 9 is a graph which illustrates a light receiving intensity of fluorescence, and a calculation result of the half-value width of the reflected light.

DESCRIPTION OF EMBODIMENTS

Figure 2:
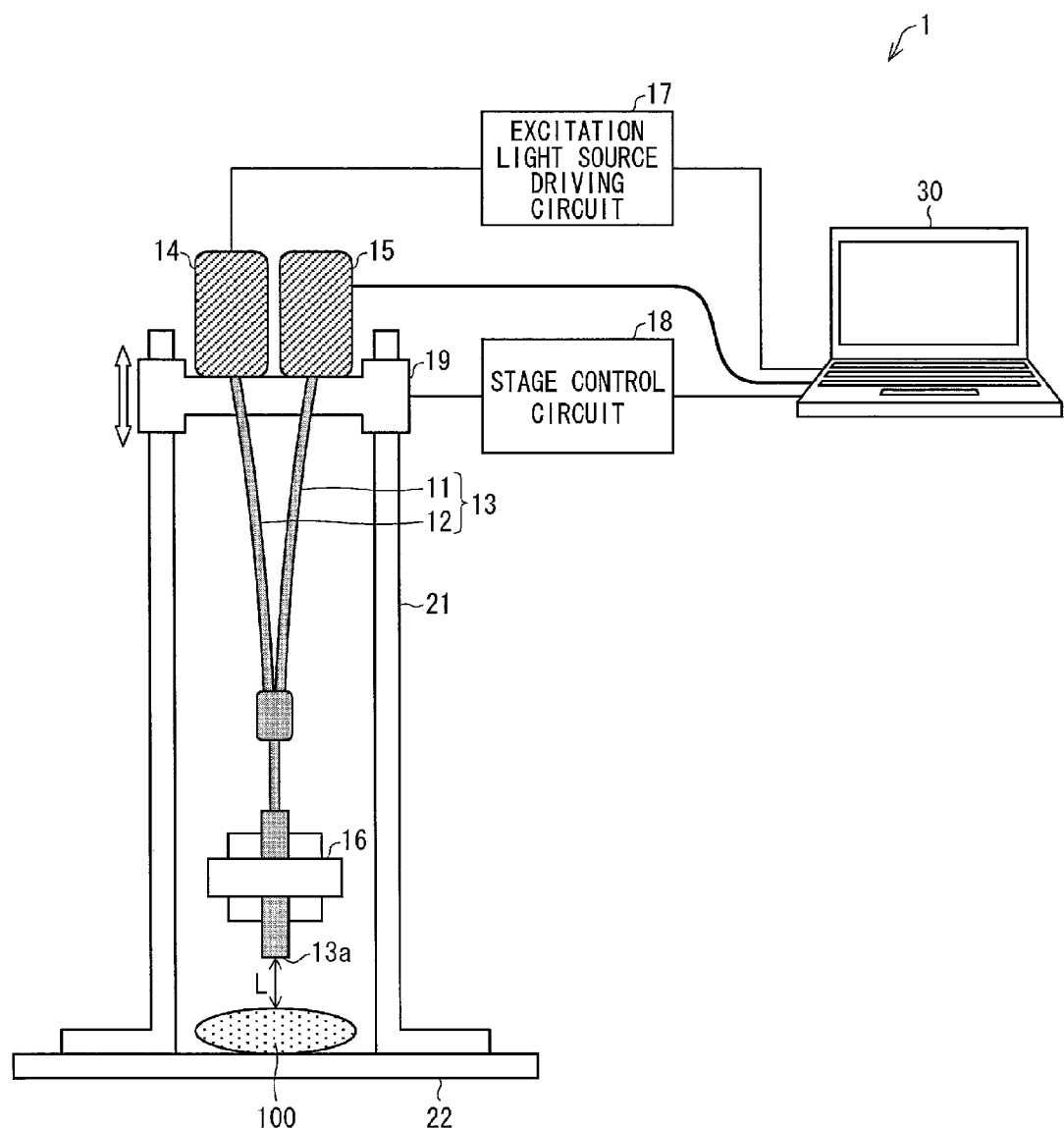
FIG. 2 is a diagram which illustrates a schematic configuration of the detection device.

Embodiments of the present invention will be described as follows based on drawings. In addition, the same or corresponding portions below in drawings are given the same reference numerals, and repeated descriptions will be omitted. In addition, a dimensional relationship in the length, a size, the width, or the like is appropriately changed for clarification and simplification of drawings, and real dimensions are not denoted.

First Embodiment

A detection device according to a first embodiment is a detection device which irradiates a test subject with excitation light, receives fluorescence which is generated due to this, and detects the fluorescence.

The detection device is mounted on a measuring system which irradiates a part of a test subject as a measuring target with excitation light, and measures an accumulated amount of AGEs (amount of fluorescence material) of a measuring target portion by analyzing obtained fluorescence spectrum (fluorescence characteristics). The detection device is mounted on the measuring system, and detects fluorescence which is radiated from a part of the body of the test subject.

It is needless to say that the detection device is able to also use an inanimate object with no vital function as a test subject, not only a living thing such as a human being, or an animal.

FIG. 2 is a diagram which illustrates a schematic diagram of a detection device 1 according to one embodiment of the present invention. As illustrated in FIG. 2, the detection device 1 includes a probe 13 which can guide excitation light which is radiated to a test subject 100, and fluorescence which is radiated from the test subject 100, a excitation light source 14 which outputs excitation light, a detector 15 which is able to detect fluorescence and reflected light, a holder 16 which maintains the probe 13, a excitation light source driving circuit 17 which drives the excitation light source, a stage control circuit (control mechanism) 18 for moving the probe 13, a stage (control mechanism) 19 of which a movement is controlled by the stage control circuit 18, a support fixture 21 which supports the stage 19 to be movable, a setting stand 22 at which the test subject 100 is set, and a control device 30 which controls a detecting operation of the detection device 1.

(Probe 13)

The probe 13 includes a reflection fiber 11 which guides fluorescence which is radiated from a test subject 100, and an input fiber 12 which guides excitation light which is radiated to the test subject 100.

An end portion of the reflection fiber 11 on the test subject 100 side faces the test subject 100, and fluorescence which is radiated from the test subject 100 is input from the end portion. The input fluorescence is propagated to the detector 15 through the reflection fiber 11. Such an end portion of the test subject 100 functions as a light receiving portion 13a which receives fluorescence which is generated when irradiating a test subject with excitation light over a plurality of detecting chances.

In addition, the reflection fiber 11 is joined to the detector 15 through an SMA connector at an end portion thereof on the detector 15 side. Fluorescence which is propagated to the reflection fiber 11 is output to the detector 15 from the end portion on the detector 15 side.

As the reflection fiber 11, for example, it is possible to use an optical fiber. By adopting the optical fiber, it is possible to guide the fluorescence to the detector 15 from the test subject 100 side without losing the fluorescence, as possible.

An end portion of the input fiber 12 on the test subject 100 side faces the test subject 100, and excitation light which is radiated to the test subject 100 is output from the end portion. Such an end portion on the test subject 100 side functions as a light irradiation portion 13a which irradiates a test subject with excitation light over a plurality of detecting chances.

In addition, an end portion of the input fiber 12 on the excitation light source 14 side is joined to the excitation light source 14 through an SMA connector. The excitation light which is output from the excitation light source 14 is input to the input fiber 12 from the end portion on the excitation light source 14 side.

As the input fiber 12, for example, it is possible to use an optical fiber. By adopting the optical fiber, it is possible to guide the excitation light to the test subject 100 side from the excitation light source 14 side without losing the fluorescence, as possible.

Both the end portion of the reflection fiber 11 on the test subject 100 side and the end portion of the input fiber 12 on the test subject 100 side are maintained using the holder 16 which is a tubular member into which a part of the reflection fiber 11, and a part of the input fiber 12 are inserted, respectively. When the reflection fiber 11 and the input fiber 12 are flexible, it is difficult to perform accurate positioning thereof, respectively. For this reason, receiving of fluorescence from the test subject 100, and irradiation of excitation light with respect to the test subject 100 are performed in a state in which the reflection fiber 11 and the input fiber 12 are inserted into the holder 16.

The holder 16 can move along the support fixture 21, and the movement is integrally performed along with a movement of the stage 19 which will be described later. For this reason, it is possible to move the holder 16 by controlling the movement of the stage 19, that is, it is possible to move each end portion (light receiving unit and irradiation unit) of the reflection fiber 11 and the input fiber 12 on the test subject 100 side.

(Excitation Light Source 14)

The excitation light source 14 is a light source which generates excitation light which is radiated to a test subject. As a type of a light source which is used as the excitation light source 14, there is a pipe ball type such as a halogen light source, or a xenon light source, an LED, an LD, or the like.

The excitation light source 14 is able to switch or adjust conditions of a wavelength which is emitted, an output intensity, an irradiation time, and the like of excitation light. The switching or adjusting of the conditions can be performed using the excitation light source driving circuit 17 which will be described later.

The excitation light source 14 is not particularly limited when it has a structure in which irradiation can be performed with a plurality of wavelengths, and it is possible to an LD (Laser Diode) in addition to an LED, a light source unit in which the LD and LED are integrated, a halogen lamp, or the like, as the excitation light source.

(Detector 15)

The detector 15 detects fluorescence which is generated when irradiating a test subject with excitation light through the reflection fiber 11 of the probe 13. The detector 15 outputs the detection result to the control device 30. As the detector 15, it is possible to use a semiconductor detector such as a CCD array, or a CMOS image sensor, a photoelectron-multiplier tube (PMT), a channeltron detector, or the like. It is advantageous when using the semiconductor detector as the detector, in order to increase portability of the detection device 1.

In addition, the detector 15 may include a spectroscope.

(Excitation Light Source Driving Circuit 17)

The excitation light source driving circuit 17 is a circuit which switches and/or adjusts a wavelength, an output intensity, and/or conditions of an irradiation time or the like of the excitation light which is output from the excitation light source 14. The excitation light source driving circuit 17 drives the excitation light source 14 by outputting a driving current which is necessary when the excitation light source 14 outputs excitation light, to the excitation light source 14. The excitation light source driving circuit 17 adjusts a presence or absence of an output, a current value thereof, a cycle, and/or an amplitude, or the like of the driving current, and executes switching or adjusting of the above described wavelength, output intensity, conditions of irradiation time, or the like of the excitation light.

Such adjusting of the driving current by the excitation light source driving circuit 17 is controlled by the control device 30 which will be described later.

(Stage Control Circuit 18 and Stage 19)

The stage 19 is arranged with, for example, the excitation light source 14 and the detector 15 thereon. Both the input fiber 12 which is joined to the excitation light source 14 and the reflection fiber 11 which is joined to the detector 15 are led to the test subject 100 side through fiber through holes which penetrate the stage 19.

The stage 19 is movable along the longitudinal direction (vertical direction in FIG. 2) of the support fixture 21, and includes, for example, a wheel, or a gear which is driven by an electric motor. The holder 16 integrally moves along with the stage 19. For this reason, the holder 16 also moves due to a movement of the stage 19. The holder 16 maintains each end portion of the reflection fiber 11 and the input fiber 12 on the test subject 100 side. Due to a movement of the holder 16, each end portion, that is, the light receiving portion and the irradiation portion 13*a* (hereinafter, simply referred to as "light receiving portion 13*a*") of the invention of the present application moves. Due to the movement of the light receiving portion 13*a*, a relative position between the light receiving portion 13*a* and the test subject 100 (here, distance L) is changed.

The stage control circuit 18 controls such a movement of the stage 19. The stage control circuit 18 is able to measure a position of the stage 19 at the support fixture 21 in the longitudinal direction. For example, the stage control circuit 18 may measure a position of the stage 19 from a rotation amount of the wheel, or the gear which is provided in the stage 19.

As described above, the stage 19 and the holder 16 integrally move. A relative position between the stage 19 and the holder 16, a relative position between the holder 16 and the end portion of the reflection fiber 11 on the test subject 100 side, and a relative position between the holder 16 and the end portion of the input fiber 12 on the test subject 100 side are measured in advance, respectively, and each interval is fixed. Accordingly, the stage control circuit 18 is able to measure the relative position between the light receiving portion 13*a* and the test subject 100 (distance L) by measuring a position of the stage 19.

Such a movement control of the stage 19, and measuring of the relative position by the stage control circuit 18 is controlled by the control device 30 which will be described later.

(Support Fixture 21)

The support fixture 21 is a fixture which supports the holder 16 and the stage 19 while moving thereof above the test subject 100. The support fixture 21 is arranged above the setting stand 22 at which the test subject 100 is set.

The support fixture 21 may be provided with a movement guiding groove (not shown) so that the holder 16 and the stage 19 are movable along the longitudinal direction thereof. The holder 16 and the stage 19 can move with high precision by adopting the movement guiding groove.

As a material of the support fixture 21, it is possible to use any of a plastic material such as light shielding polystyrene, or polyethylene, container paper which is added with aluminum foil inside, a metal material, a wood material, or the like, however, it is advantageous when using the light shielding plastic, when considering portability, profitability, and endurance.

(Setting Stand 22)

The setting stand 22 is a stand at which the test subject 100 is set. It is necessary for the setting stand 22 to have a property of not being changed in a shape thereof due to a change in circumstances or the like in order to precisely measure the relative position between the light receiving unit 13*a* and the test subject 100. In addition, a setting surface on which the test subject 100 is set is required to have high flatness.

(Control Device 30)

FIG. 1 is a block diagram which illustrates a configuration of the control device 30 of the detection device 1. As illustrated in FIG. 1, the control device 30 includes a setting unit (adjusting means) 31, a light receiving intensity calculation unit (light receiving intensity calculation means) 32, a specifying unit (specifying means) 33, an informing unit (informing means) 34, a display unit 35, and a storage unit 36.

The setting unit 31 executes various setting with respect to the excitation light source driving circuit 17, the detector 15, and the stage control circuit 18. First, the setting unit 31 sets each operation timing so that driving of the excitation light source 14 by the excitation light source driving circuit 17, detecting of fluorescence by the detector 15, and moving of the stage 19 by the stage control circuit 18 are synchronous.

Specifically, the setting unit 31 moves the stage 19 using the stage control circuit 18, and changes a relative position between the light receiving portion 13*a* and the test subject 100. A moving range of the stage 19 is predetermined, and for example, is stored in the storage unit 36.

In addition, the setting unit 31 adjusts a driving current which is output to the excitation light source 14 using the excitation light source driving circuit 17 while changing the relative position. The driving current is adjusted so that excitation light in a certain wavelength range is repeatedly output from the excitation light source 14 while changing the relative position. The wavelength range is predetermined, and for example, is stored in the storage unit 36.

That is, the setting unit 31 causes the excitation light in the wavelength range to be output from the excitation light source 14 in each relative position each time a relative position between the light receiving portion 13*a* and the test subject 100 is changed. For example, when the relative position comes to a predetermined position the excitation light in the wavelength range may be output. The predetermined position can select, for example, an arbitrary position in the moving range.

In addition, the setting unit 31 causes the detector 15 to detect fluorescence which is received by the light receiving portion 13*a* when the excitation light in the wavelength range is caused to output from the excitation light source 14 in a certain relative position. The detecting of fluorescence by the detector 15 is performed each time the relative position is changed, and is performed relating to the respective excitation light in the wavelength range.

In addition, the setting unit 31 may adjust an output intensity of excitation light.

Each time the detector 15 detects fluorescence which is received by the light receiving portion 13*a*, the light receiving intensity calculation unit 32 obtains a detection result thereof. The light receiving intensity calculation unit 32 calculates a light receiving intensity of fluorescence in a certain wavelength range in one relative position using the detection result. As described above, in the moving range, a plurality of the relative positions for receiving fluorescence are determined. For this reason, the light receiving intensity calculation unit 32 calculates a light receiving intensity of fluorescence in a certain wavelength range with respect to each of the plurality of relative positions. In addition, the "certain wavelength range" of fluorescence depends on a wavelength range of excitation light which is radiated to the test subject 100, and a material which gives off fluorescence which is included in the test subject 100.

Here, the "light receiving intensity" is a peak value of fluorescence which is received by the light receiving portion 13a, and it is known that the peak value changes according to a change in a relative position between the light receiving portion 13a and the test subject 100.

The specifying unit 33 obtains a position of the stage 19 which is measured by the stage control circuit 18, that is, a relative position (distance L) between the light receiving portion 13a and the test subject 100 from the stage control circuit 18. In addition, relating to each of the plurality of relative positions, the specifying unit 33 obtains the light receiving intensity of the fluorescence in the wavelength range from the light receiving intensity calculation unit 32.

As described above, timings of the respective operations of the excitation light source driving circuit 17, the detector 15, and the stage control circuit 18 are synchronous. For this reason, the specifying unit 33 obtains the light receiving intensity of the fluorescence in the wavelength range corresponding to each of the plurality of relative positions.

The specifying unit 33 finds out the maximum light receiving intensity among the light receiving intensities of the fluorescence in the wavelength range which corresponds to each of the plurality of relative positions, and which are obtained in this manner. In addition, the specifying unit 33 specifies an optimal position which is a relative position corresponding to the maximum light receiving intensity. The optimal position is optimal as a relative position between the light receiving portion 13a and the test subject 100.

That is, it is possible to make the light receiving intensity of fluorescence which is received by the light receiving portion 13a maximum using the optimal position in a relative position between the light receiving portion 13a and the test subject 100, and as a result, it is possible to detect fluorescence with high precision. The specifying unit 33 stores the optimal position which is specified in this manner in the storage unit 36.

When the light receiving intensity calculation unit 32 is not able to calculate a light receiving intensity of fluorescence using a detection result of the detector 15, the informing unit 34 informs of the fact.

For example, when the light receiving intensity calculation unit 32 is not able to calculate a light receiving intensity of fluorescence because of the extremely large light receiving intensity, there is a doubt that an output intensity of excitation light which is output from the excitation light source 14 is extremely large, or there is an interfering substance with fluorescence in the test subject 100. For this reason, the informing unit 34 informs of content of the notification "The fluorescence is too strong. Please check the intensity of excitation light, and whether or not an interfering substance is present." A user may be informed of the informing contents using the display unit 35 which will be described later. In addition, it may be informed using a sound through a speaker.

In addition, as described above, the setting unit 31 is able to adjust an output intensity of the excitation light source 14 using the excitation light source driving circuit 17. For this reason, the informing unit 34 may instruct the setting unit 31 to adjust the output intensity of the excitation light source 14 before informing of the above described informing contents. The setting unit 31 adjusts the output intensity of the excitation light source 14 so that the light receiving intensity is in an appropriate range in order to allow the light receiving intensity calculation unit 32 to calculate light receiving intensity of fluorescence. In this case, the informing contents may be informed when the light receiving intensity calculation unit 32 could not calculate the light receiving intensity even after performing the adjusting of the output intensity of the excitation light source 14. In addition, the setting unit 31 may adjust a relative position between the light receiving portion 13a and the test subject 100, not adjusting the output intensity of the excitation light source 14. In this case, for example, the stage control circuit 18 may move a position of the stage 19 under a control of the setting unit 31.

On the other hand, when the light receiving intensity calculation unit 32 is not able to calculate a light receiving intensity of fluorescence because of a too small light receiving intensity, there is a doubt that the output intensity of excitation light which is output from the excitation light source 14 is too small, a relative position between the light receiving portion 13a and the test subject 100 is too large, or there is a substance which absorbs excitation light in the test subject 100. For this reason, the informing unit 34 informs contents of "The fluorescence is not detected. Please check the intensity of excitation light, a detection place, or whether or not an interfering substance is present." A user may be informed of the informing contents using the display unit 35 which will be described later. In addition, it may be informed using a sound through a speaker.

In addition, in this case, as well, the informing unit 34 may instruct the setting unit 31 to adjust the output intensity of the excitation light source 14 before informing the above described informing contents. In addition, the above described informing contents may be informed when it is possible to calculate the light receiving intensity by the light receiving intensity calculation unit 32, even after adjusting the output intensity of the excitation light source 14.

In addition, when the moving range is not appropriate, or a setting position of the test subject 100 is moved, there is a doubt that there is deviation in a detection portion due to a variation in a setting position of the test subject 100, or the optimal position is present out of the moving range. For this reason, the informing unit 34 informs of contents of "It is not possible to specify the fluorescence detection position. Please check the detection position, and the moving range." A user may also be informed of the informing contents using the display unit 35 which will be described later. In addition, it may be informed using a sound through a speaker.

The display unit 35 displays a light receiving intensity of fluorescence which is calculated by the light receiving intensity calculation unit 32, and informing contents which are received by the informing unit 34. The display unit 35 is configured by a display device, for example, an LCD (liquid crystal display), or the like.

The storage unit 36 is configured by a non-volatile storage device such as a hard disk, a flash memory, or the like. The storage unit 36 stores the moving range of the stage 19, a wavelength range of excitation light which is output from the excitation light source 14, and an optimal position which is specified by the specifying unit 33. The setting unit 31 can be obtained such as information described above from the storage unit 36.

(Calculation Result of Light Receiving Intensity Calculation Unit 32)

FIG. 3 illustrates an example of a calculation result of a light receiving intensity of fluorescence by the light receiving intensity calculation unit 32 in the wavelength range in each of the plurality of relative positions. In FIG. 3, the plurality of relative positions are four of I1, I2, I3, and I4. As illustrated in FIG. 3, when the relative position is I1, the light receiving intensity is the maximum (portion A illustrated in figure) in the example of the result. The relative position I1 is the optimal position.

That is, the specifying unit 33 finds out a maximum light receiving intensity among the plurality of relative positions I1, I2, I3, and I4, and specifies the relative position I1 corresponding to the light receiving intensity as the optimal position.

(Flow of Processing of Control Device 30)

Figure 10:
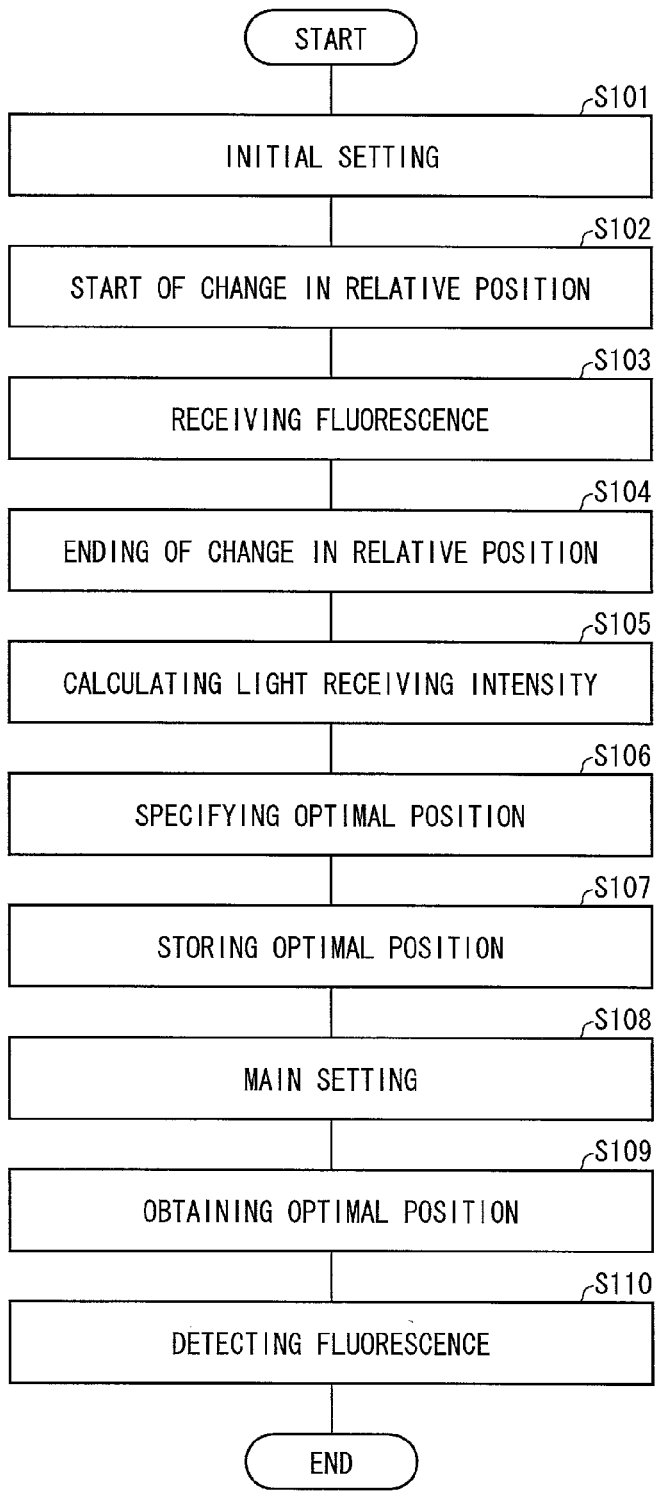
FIG. 10 is a flowchart which illustrates an example of a flow of processing of a control device of the detection device according to an embodiment of the present invention.

Subsequently, an example of a flow of processing in the control device 30 will be described. FIG. 10 is a flowchart which illustrates an example of the processing in the control device 30.

In FIG. 10, first, the setting unit 31 performs initial setting of the detector 15, the excitation light source driving circuit 17, and the stage control circuit 18 (step S101). In the step S101, the setting unit 31 sets detection resolution when detecting fluorescence with respect to the detector 15. The detection resolution in the initial setting is compared to detection resolution in main setting which will be described later, and is set to be the same, or lower than that. In this manner, it is possible to reduce time which is necessary for a detecting process in the detector 15.

In addition, the setting unit 31 sets an output intensity of excitation light which is output from the excitation light source 14 with respect to the excitation light source driving circuit 17. The output intensity of excitation light in the initial setting is compared to an output intensity of excitation light in the main setting which will be described later, and is set to be the same, or lower than that. In this manner, it is possible to suppress a degree of damage to the test subject 100 due to irradiation of excitation light.

Further, the setting unit 31 sets a moving start position of the stage 19 in the moving range of the stage 19, and a moving end position of the stage 19 in the moving range of the stage 19, respectively, with respect to the stage control circuit 18. The stage 19 moves to the moving end position from the moving start position. Due to the movement of the stage 19, a relative position between the light receiving portion 13a and the test subject 100 is changed.

When the initial setting by the setting unit 31 is finished, the stage control circuit 18 starts to move the stage 19. That is, a change in a relative position between the light receiving portion 13a and the test subject 100 is started (step S102). In the step S102, when a change in the relative position is started, driving of the excitation light source 14 by the excitation light source driving circuit 17, and detecting of fluorescence by the detector 15 are started along with the start thereof. In addition, as described above, the stage control circuit 18 outputs a measured position of the stage 19, that is, the relative position between the light receiving portion 13a and the test subject 100 to the specifying unit 33 each time a relative position is changed.

When the relative position starts to change, excitation light in the wavelength range is output by the excitation light source 14 in each of the relative position each time the relative position is changed. The excitation light in the wavelength range is output to the test subject 100 in each relative position, and the test subject 100 radiates fluorescence. The light receiving portion 13a receives the fluorescence which is radiated by the test subject 100 (step S103). In the step S103, the detector 15 detects the fluorescence which is received by the light receiving portion 13a. The detection of the fluorescence by the detector 15 is performed each time the relative position is changed, and is performed with respect to the each fluorescence in the wavelength range.

The stage control circuit 18 finishes the movement of the stage 19 when the stage 19 moves in the moving range, and reaches the movement end position. That is, the change in the relative position is finished (step S104). In the step S104, when the change in the relative position is finished, driving of the excitation light source 14 by the excitation light source driving circuit 17, and detecting of fluorescence by the detector 15 are finished along with the ending thereof.

The light receiving intensity calculation unit 32 receives the detection result of the detector 15, and calculates the light receiving intensity of fluorescence in a certain wavelength range with respect to each relative position in the moving range (step S105). In the step S105, when the light receiving intensity calculation unit 32 is not able to calculate the light receiving intensity of fluorescence using the detection result of the detector 15, as described above, the fact is informed.

The specifying unit 33 finds out the maximum light receiving intensity among light receiving intensities of fluorescence in the wavelength range corresponding to each of the plurality of relative positions. In addition, the specifying unit 33 specifies the optimal position as the relative position which corresponds to the maximum light receiving intensity (step S106). In addition, the specifying unit 33 stores the specified optimal position in the storage unit 36 (step S107).

When the specifying unit 33 specifies the optimal position, the setting unit 31 performs main setting of the detector 15, the excitation light source driving circuit 17, and the stage control circuit 18 (step S108). In the step S108, the setting unit 31 sets detection resolution when detecting fluorescence with respect to the detector 15, similarly to the initial setting in the step S101. However, the detection resolution in the main setting is compared to the detection resolution in the initial setting, and is set to be larger than that. In this manner, it is possible to improve precision in a detecting processing of the detector 15.

In addition, the setting unit 31 sets an output intensity of excitation light which is output from the excitation light source 14 with respect to the excitation light source driving circuit 17, similarly to the initial setting in the step S101. However, the output intensity of the excitation light in the main setting is set to be higher than the output intensity of the excitation light in the initial setting. In this manner, it is possible to improve precision in the detecting processing of the detector 15 since amount of fluorescence which is radiated from the test subject 100 due to irradiation of excitation light is increased.

In addition, the setting unit 31 sets the moving range of the stage 19, and a position of the stage 19 in the moving range with respect to the stage control circuit 18. Specifically, the setting unit 31 obtains an optimal position from the storage unit 36, and sets a position of the stage 19, that is, a relative position between the light receiving portion 13a and the test subject 100 as the optimal position (step S109).

In this manner, a relative position between the light receiving portion 13a and the test subject 100 is set as the optimal position, and the detector 15 performs detecting of fluorescence (step S110). In addition, in the step S110, when the light receiving intensity calculation unit 32 is not able to calculate light receiving intensity of fluorescence using the detection result of the detector 15, or the light receiving intensity becomes unstable, there is a doubt that a detection portion is deviated due to a variation in a setting position of the test subject 100, or there is an abnormality in the optical system of the detection device 1. For this reason, the informing unit 34 informs of informing contents of "Fluorescence detecting has failed. Please check the detection portion, and the optical system."

As described above, according to the detection device 1 in the embodiment, when detecting fluorescence which is radiated from a test subject, it is possible to make a light receiving intensity of a light receiving unit maximum without using a special additional mechanism. Due to this, it is possible to detect fluorescence with high precision, and inexpensively.

Modification Example

Figure 11:
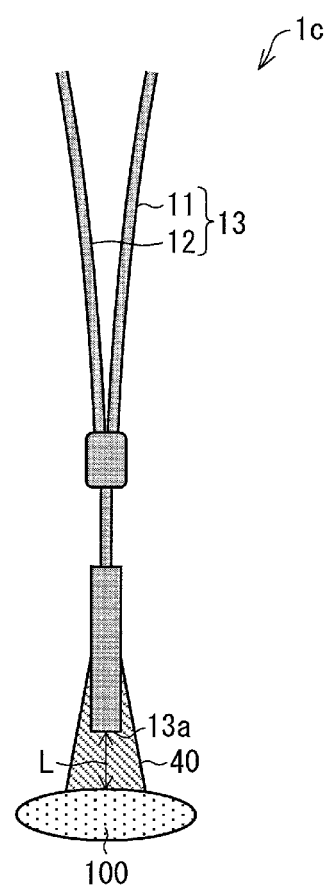
FIG. 11 is an explanatory diagram which describes a function of a member of a fixing unit.

FIG. 11 is a schematic diagram which describes a fixing member 40 which fixes a relative position between the light receiving portion 13a and the test subject 100 to the optimal position. The fixing member 40 is a member which is interposed between a light receiving portion 13a and a test subject 100 so that a relative position between the light receiving portion 13a and the test subject 100 (distance L) becomes an optimal position.

As described above, the optimal position is specified by a specifying unit 33 of a control device 30. The fixing member 40 may be manufactured using a material, for example, metal or the like of which a shape thereof is not changed due to a change in circumstances using the specified optimal position.

A user is able to easily set the relative position between the light receiving portion 13a and the test subject 100 to the optimal position by manufacturing the fixing member 40, after the optimal position is specified, once.

Figure 12:
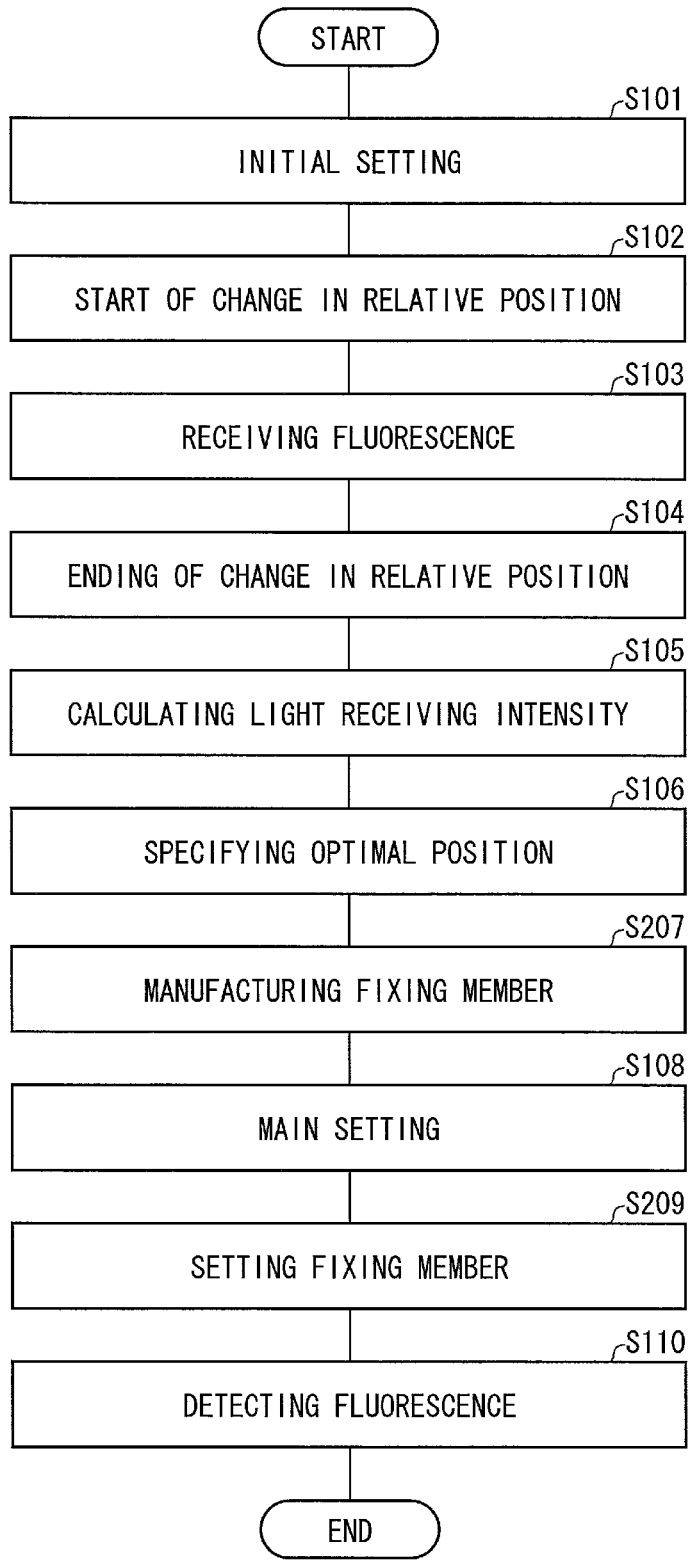
FIG. 12 is a flowchart which illustrates an example of a flow of processing of a control device of the detection device according to another embodiment of the present invention.

FIG. 12 is a flowchart which illustrates an example of a flow of processing in the control device 30 when the fixing member 40 is used. As illustrated in FIG. 12, the fixing member 40 is manufactured after the steps S101 to S106 in FIG. 10 (step S207). In addition, after the step S108, the fixing member 40 is set (step S209).

Second Embodiment

According to the first embodiment, the distance L between the light receiving portion 13a and the test subject 100 has been used as an index which denotes a relative position between the light receiving portion 13a and the test subject 100. In contrast to this, according to a second embodiment of the present invention, as an index which denotes the relative position between the light receiving portion 13a and the test subject 100, a pressure which is generated between the light receiving portion 13a and the test subject 100.

Figure 4:
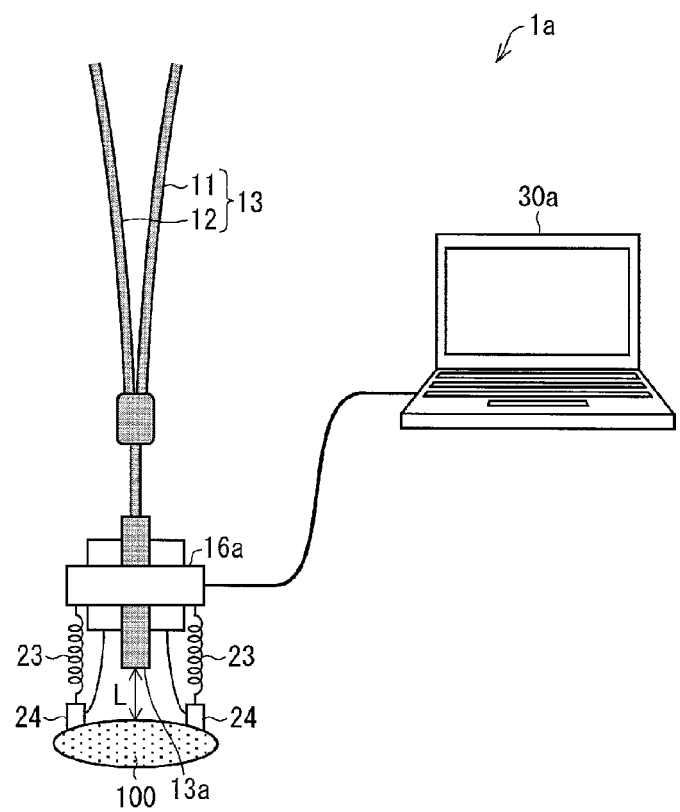
FIG. 4 is a diagram which illustrates a schematic configuration of a detection device according to another embodiment of the present invention.
Figure 5:
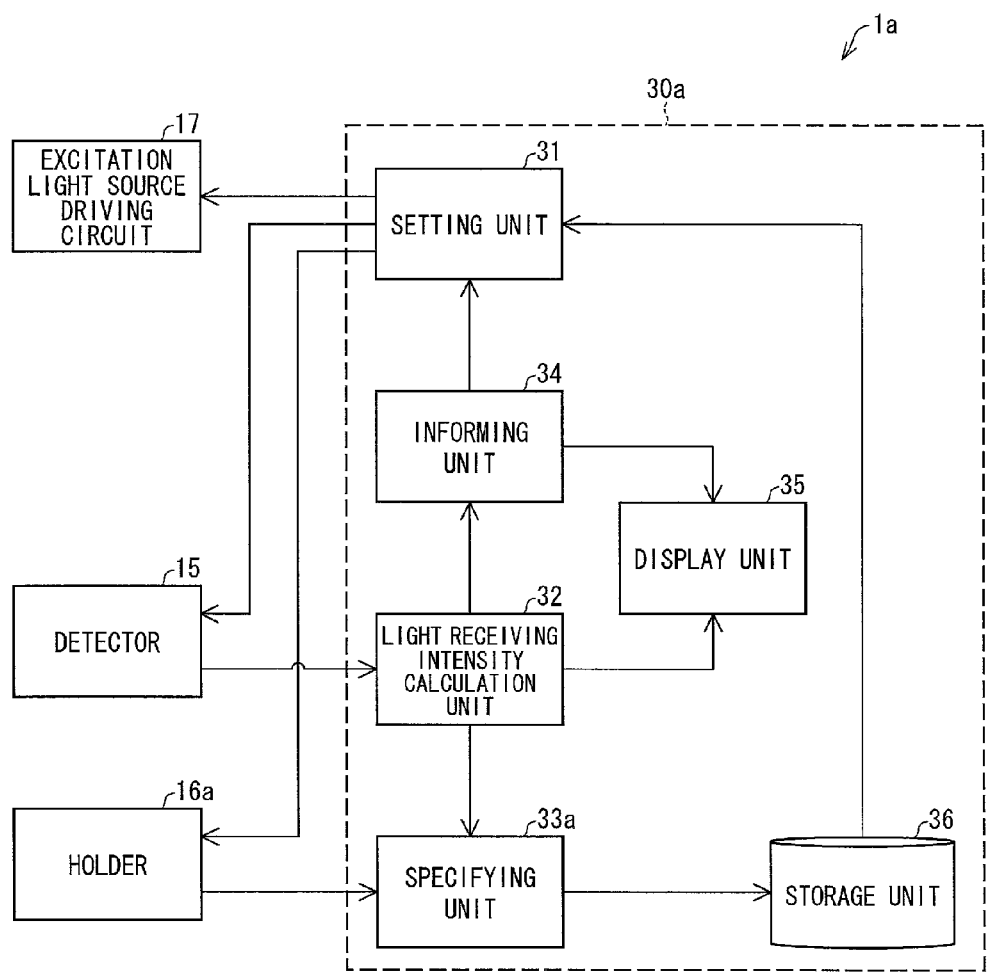
FIG. 5 is a block diagram which illustrates a configuration of the detection device.

Hereinafter, a configuration thereof will be described using drawings. FIG. 4 is a diagram which illustrates a schematic configuration of a detection device 1a according to the second embodiment of the present invention. In addition, FIG. 5 is a block diagram which illustrates a configuration of a control device 30a of the detection device 1a. Hereinafter, the same portions as those in the first embodiment will be given the same reference numerals, and detailed descriptions thereof will be omitted.

As illustrated in FIGS. 4 and 5, a different point in the detection device 1a according to the embodiment from the detection device 1 in the first embodiment is that an elastic body (detection unit) 23 and a pressure sensor (detection unit) 24 for detecting a pressure which is generated between the light receiving portion 13a and the test subject 100 are provided. In addition, as illustrated in FIG. 4, a holder 16a is communicably connected to the pressure sensor 24, and the control device 30a differently from the holder 16 in the first embodiment. In this manner, the holder 16a is able to send out a pressure value which is detected by the pressure sensor 24 to the control device 30a using an analog signal, or a digital signal.

As illustrated in FIG. 4, in the detection device 1a, the elastic body 23 such as a spring and the pressure sensor 24 are interposed between the holder 16a and the test subject 100. In the pressure sensor 24, a pressure which is generated along with a contraction of the elastic body 23 is increased when the holder 16a comes closer to the test subject 100. The pressure sensor 24 is connected to the elastic body 23, and due to this, it is possible to detect the increase in pressure which is generated along with the contraction of the elastic body 23.

On the other hand, the pressure which is generated due to the contraction of the elastic body 23 depends on a distance between the holder 16a and the test subject 100. Further, a relative position between the holder 16a and an end portion of the reflection fiber 11 on the test subject 100 side, and a relative position between the holder 16a and an end portion of the input fiber 12 on the test subject 100 side are measured in advance, respectively, and each interval is fixed.

Accordingly, it is understood that the pressure due to the contraction of the elastic body 23 depends on a distance between the light receiving portion 13a and the test subject 100.

In addition, in FIG. 4, the elastic body 23 and the pressure sensor 24 are interposed between the holder 16a and the test subject 100, however, as a matter of course, the elastic body and the pressure sensor may be interposed between the light receiving portion 13a and the test subject 100.

In the control device 30a of the detection device 1a which is illustrated in FIG. 5, a setting unit 31 moves a stage 19 using a stage control circuit 18, similarly to the first embodiment. Due to this, a pressure which is generated between the light receiving portion 13a and the test subject 100 is changed. In brief, in the control device 30a, a relative position (distance L) between the light receiving portion 13a and the test subject 100 is denoted using a pressure therebetween.

Figure 6:
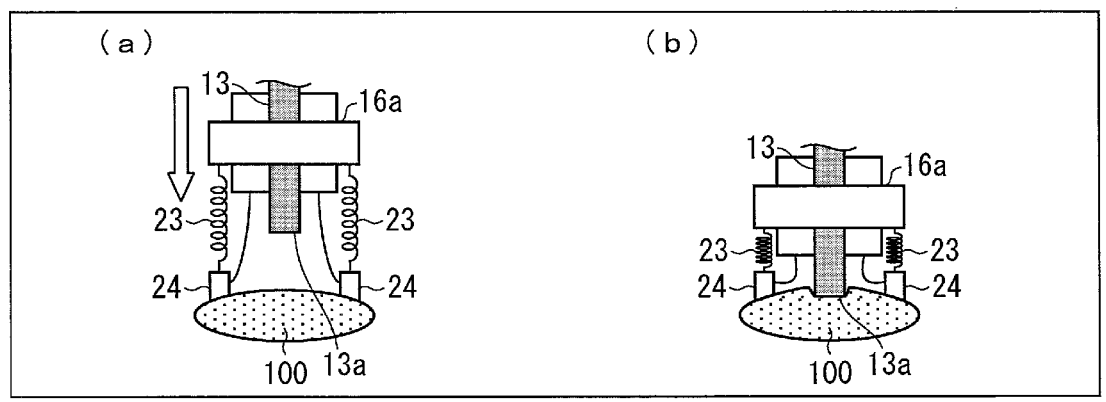
FIG. 6 is an explanatory diagram which describes functions of an elastic body and a pressure sensor of the detection device.

In addition, in the control device 30a, a specifying unit 33a is provided instead of the specifying unit 33 of the control device 30. The specifying unit 33a obtains a pressure which is detected by the pressure sensor 24. The specifying unit 33a obtains a detection result of the pressure sensor 24 through the holder 16a. For example, as illustrated in FIG. 6, a pressure which is detected by the pressure sensor 24 is increased when the state (a) comes closer to the state (b).

In addition, the specifying unit 33a obtains a light receiving intensity of fluorescence in the wavelength range from the light receiving intensity calculation unit 32 relating to each of the plurality of relative positions, similarly to the specifying unit 33.

The specifying unit 33a finds out the maximum light receiving intensity among the light receiving intensities of fluorescence in the wavelength range corresponding to each of the plurality of relative positions which is obtained in this manner. In addition, the specifying unit 33a specifies an optimal position which is a relative position corresponding to the maximum light receiving intensity. The optimal position denotes a pressure which is generated between the light receiving portion 13a and the test subject 100.

Third Embodiment

According to the second embodiment of the present invention, the relative position between the light receiving portion 13a and the test subject 100 has been denoted using the distance between the light receiving portion 13a and the test subject 100 in the first embodiment, that is, the pressure which is generated between the light receiving portion 13*a* and the test subject 100 in the second embodiment. In contrast to this, a third embodiment of the present invention is an embodiment in which a relative position between a light receiving portion 13*a* and a test subject 100 is denoted using a half-value width of reflected light as excitation light which is reflected by the test subject 100 among excitation light beams which are irradiated to the test subject 100, as an index which denotes a relative position between the light receiving portion 13*a* and the test subject 100.

Figure 7:
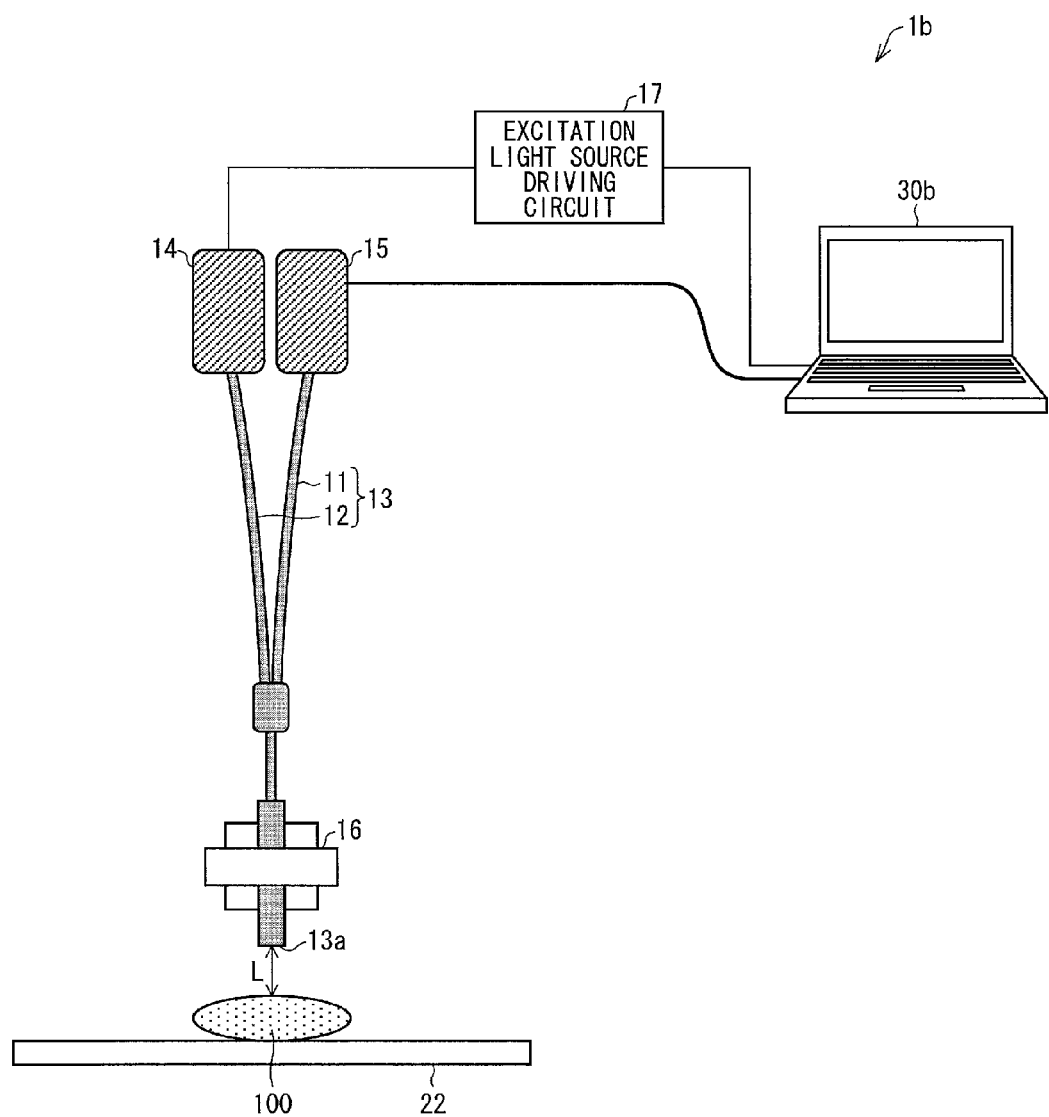
FIG. 7 is a diagram which illustrates a schematic configuration of a detection device according to still another embodiment of the present invention.
Figure 8:
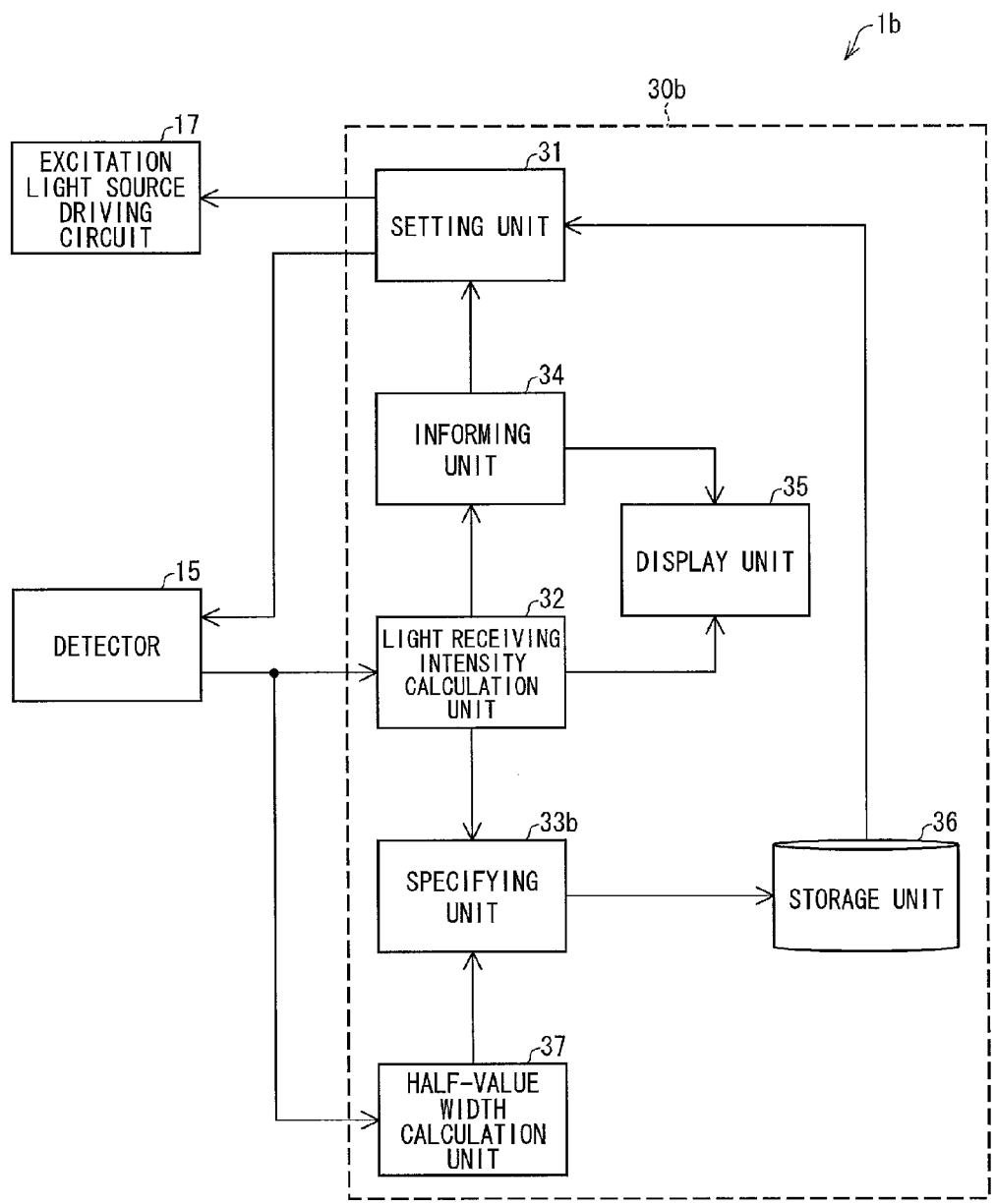
FIG. 8 is a block diagram which illustrates a configuration of the detection device.

Hereinafter, a configuration thereof will be described using drawings. FIG. 7 is a schematic diagram which illustrates a schematic configuration of a detection device 1*b* according to the third embodiment of the present invention. In addition, FIG. 8 is a block diagram which illustrates a configuration of a control device 30*b* of a detection device 1*b*. Hereinafter, the same portions as those in the first and second embodiments are given the same reference numerals, and detailed descriptions thereof will be omitted.

As illustrated in FIGS. 7 and 8, in the detection device 1*b*, excitation light which is reflected by a test subject 100, and is input to a reflection fiber 11 from a light receiving portion 13*a*, that is, reflected light is present among excitation light beams which are output from an excitation light source 14. Differences in the detection device 1*b* according to the embodiment from the detection device 1 in the first embodiment are that the reflected light is detected by a detector 15, and the control device 30*b* of the detection device 1*b* is provided with a half-value width calculation unit (half-value width calculation means) 37 which calculates the half-value width of the reflected light. Due to this, it is not necessary to provide a measuring mechanism for measuring positions of a stage control circuit 18 and a stage 19, and it is possible to detect fluorescence at a cheaper cost.

As illustrated in FIG. 8, the control device 30*b* of the detection device 1*b* includes the half-value width calculation unit 37 which calculates the half-value width of reflected light from a detection result of the detector 15. Each time the detector 15 detects reflected light which is received by the light receiving portion 13*a*, the half-value width calculation unit 37 obtains the detection result. The half-value width calculation unit 37 calculates a light receiving intensity of reflected light at a certain wavelength range in one relative position using the detection result. In addition, the half-value width calculation unit 37 calculates the half-value width of reflected light in a certain wavelength range relating to a plurality of the relative positions. In addition, "a certain wavelength range" of the reflected light depends on the wavelength range of excitation light which is radiated to the test subject 100, and the surface state of the test subject 100.

In addition, in the control device 30*b*, a specifying unit 33*b* is provided instead of the specifying unit 33 of the control device 30. The specifying unit 33*b* obtains the half-value width of reflected light which is calculated by the half-value width calculation unit 37. In addition, the specifying unit 33*b* obtains the light receiving intensity of fluorescence in the wavelength range from the light receiving intensity calculation unit 32 with respect to each of the plurality of relative positions, similarly to the specifying unit 33.

The specifying unit 33*b* finds out a maximum light receiving intensity among light receiving intensities of fluorescence in the wavelength range corresponding to the respective plurality of relative positions which are obtained in this manner. In addition, the specifying unit 33*b* specifies an optimal position which is a relative position corresponding to the maximum light receiving intensity. The optimal position is denoted using the half-value width of reflected light which is received by the light receiving portion 13*a*.

(Calculation Result of Light Receiving Intensity Calculation Unit 32 and Half-Value Width Calculation Unit 37)

FIG. 9 illustrates an example of a result of calculating a light receiving intensity of fluorescence in the wavelength range in each of the plurality of relative positions by the light receiving intensity calculation unit 32. FIG. 9 further illustrates an example of calculating the half-value width of a reflected light in the wavelength range in each of the plurality of relative positions by the half-value width calculation unit 37, as well. In FIG. 9, the plurality of relative positions are four of I1, I2, I3, and I4.

As illustrated in FIG. 9, in the examples of results, when the relative position is I1, the light receiving intensity becomes the maximum (portion denoted by B in figure). The relative position I1 is the optimal position. In addition, the half-value width denoted by the relative position 11 is the half-value width which is denoted by C in the figure.

That is, the specifying unit 33*b* finds out the maximum light receiving intensity among the plurality of relative positions I1, I2, I3, and I4, and specifies the half-value width which denotes the relative position I1 corresponding to the light receiving intensity as the optimal position.

(Flow of Processing of Control Device 30*b*)

Figure 13:
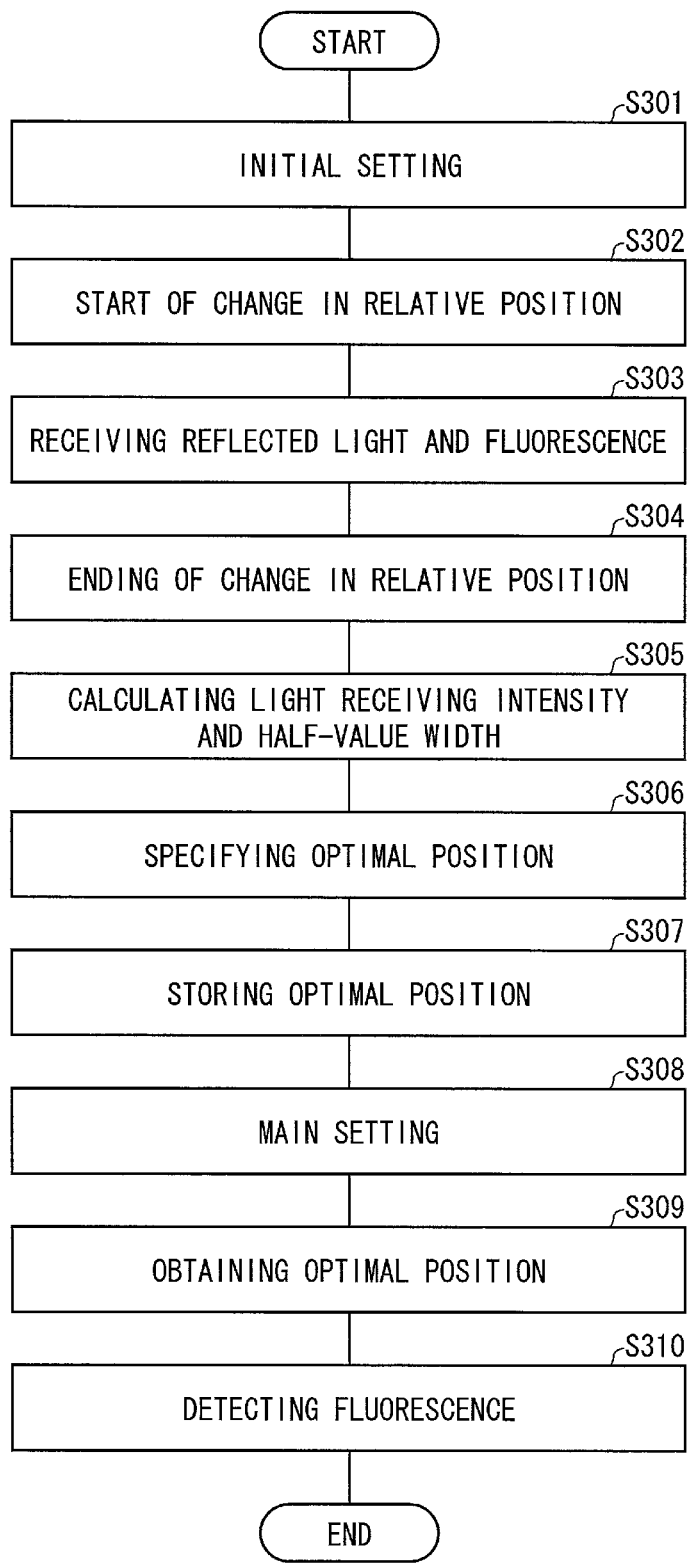
FIG. 13 is a flow chart which illustrates an example of a flow of processing of a control device of the detection device according to still further another embodiment of the present invention.

Subsequently, an example of a flow of processing of the control device 30*b* will be described. FIG. 13 is a flowchart which denotes an example of a flow of the processing in the control device 30*b*.

In FIG. 13, first, the setting unit 31 performs an initial setting of the detector 15 and the excitation light source driving circuit 17 (step S301). In the step S301, the setting unit 31 sets a detection resolution at the time of detecting fluorescence and reflected light with respect to the detector 15. The detection resolution in the initial setting is compared to a detection resolution in the main setting which will be described later, and is set to be the same or lower than that. By doing so, it is possible to shorten a time which is necessary for the detecting processing in the detector 15.

In addition, the setting unit 31 sets an output intensity of excitation light which is output from the excitation light source 14 with respect to the excitation light source driving circuit 17. The output intensity of the excitation light in the initial setting is compared to an output intensity of excitation light in the main setting which will be described later, and is set to be the same or lower than that. By doing so, it is possible to suppress a degree of damage to the test subject 100 due to irradiation of excitation light to be low.

When the initial setting by the setting unit 31 is finished, a user starts to move the light receiving unit 13*a*. That is, a change in a relative position between the light receiving unit 13*a* and the test subject 100 is started (step S302). In the step S302, when the change in the relative position is started, driving of the excitation light source 14 by the excitation light source driving circuit 17, and detecting of fluorescence and reflected light by the detector 15 are started along with the start.

When the change in the relative position is started, excitation light in the wavelength range is output from the excitation light source 14 in each relative position, each time the half-value width of the reflected light which denotes the relative position is changed. In each relative position, excitation light in the wavelength range is output to the test subject 100, and the test subject 100 radiates fluorescence. The light receiving unit 13*a* receives the fluorescence which is radiated from the test subject 100. In addition, the light receiving unit 13*a* also receives reflected light which is reflected from the test subject 100 (step S303). In the step S303, the detector 15 detects the fluorescence and the reflected light which are received by the light receiving unit 13a. The detecting of the fluorescence and the reflected light by the detector 15 is performed each time the relative position is changed, and is performed with respect to each of the excitation light beams in the wavelength range.

The user finishes the movement of the light receiving unit 13a. That is, the change in the relative position is finished (step S304). In the step S304, when the change in the relative position is finished, driving of the excitation light source 14 by the excitation light source driving circuit 17, and detecting of fluorescence and reflected light by the detector 15 are finished along with the finishing.

The light receiving intensity calculation unit 32 receives a detection result of the detector 15, and calculates a light receiving intensity of fluorescence in a certain wavelength range with respect to each of relative positions. On the other hand, the half-value width calculation unit 37 receives a detection result of the detector 15, and calculates a half-value width of reflected light in a certain wavelength range with respect to each of relative positions (step S305). In addition, in the step S305, when the half-value width calculation unit 37 is not able to calculate a half-value width of reflected light using the detection result of the detector 15, there is a doubt that the light receiving unit 13a and the test subject 100 are too far from each other. For this reason, the informing unit 34 informs informing contents of "Probe contact is abnormal. Please check a detection portion.".

The specifying unit 33b finds out the maximum light receiving intensity among the light receiving intensities of fluorescence in the wavelength range which correspond to each of the plurality of relative positions. In addition, the specifying unit 33a specifies an optimal position (half-value width of reflected light) which is a relative position corresponding to the maximum light receiving intensity (step S306). In addition, the specifying unit 33b stores the specified optimal position in the storage unit 36 (step S307).

When the specifying unit 33b specifies the optimal position, the setting unit 31 performs main setting of the detector 15 and the excitation light source driving circuit 17 (step S308). In the step S308, the setting unit 31 sets a detection resolution at the time of detecting fluorescence and reflected light with respect to the detector 15, similarly to the initial state of step S301. However, the detection resolution in the main setting is compared to the detection resolution in the initial setting, and is set to be larger than that. By doing so, it is possible to improve precision of the detecting processing of the detector 15.

In addition, the setting unit 31 sets an output intensity of excitation light which is output from the excitation light source 14 with respect to the excitation light source driving circuit 17, similarly to the initial setting in the step S301. However, the output intensity of excitation light in the main setting is compared to the output intensity of the excitation light in the initial setting, and is set to be larger than that. By doing so, amount of fluorescence which is radiated from the test subject 100 due to irradiation of excitation light in increased, and it is possible to improve precision of the detecting processing of the detector 15.

Further, the user obtains an optimal position from the storage unit 36, and sets the optimal position (half-value width of reflected light) of a relative position between the light receiving unit 13a and the test subject 100 (step S309). In addition, the stage control circuit 18 may be controlled so that the setting unit 31 reads out the optimal position from the storage unit 36, and the relative position between the light receiving unit 13a and the test subject 100 is set to the read out optimal position (half-value width of reflected light).

In this manner, the relative position between the light receiving unit 13a and the test subject 100 is set to the optimal position, and the detector 15 performs detecting of fluorescence (step S110).

As described above, according to the detection device 1b in the embodiment, reflected light is also received along with fluorescence using the light receiving unit, and the half-value width of reflected light which is changed according to a change in a relative position between the light receiving unit and the test subject may be calculated. For this reason, it is possible to make the detection device simple, and inexpensive.

The Other Modification Example

The present invention is not limited to the above described each embodiment, it is possible to make various modifications in claims, and embodiments which are obtained by appropriately combining technical means which are respectively disclosed in different embodiments are also included in technical ranges of the present invention.

Each block in the above described control devices 30, 30a, and 30b excepting for the display unit 35 and the storage unit 36 may be configured by hardware logic, or may be realized by software using a CPU as follows.

That is, the control devices 30, 30a, and 30b includes a storage unit (recording medium), or the like, such as a CPU (central processing unit) which executes a command of a control program which executes each function, a ROM (read only memory) which stores the program, a RAM (random access memory) which develops the program, and a memory which stores the program, and various data. In addition, an object of the present invention can be achieved by supplying a recording medium in which a program code (executable program, intermediate code program, and source program) of a control program (authentication program) of the control devices 30, 30a, and 30b which are software executing the above described functions is recorded as a computer readable code is supplied to the control devices 30, 30a, and 30b, and by reading out and executing the program code which is recorded in the recording medium by the computer (or, CPU or MPU).

As the recording medium, for example, it is possible to use tapes such as a magnetic tape, or a cassette tape, magnetic disks such as a floppy (registered trademark) disk, or a hard disk, discs including optical disc such as CD-ROM, MO, MD, DVD, or CD-R, cards such as an IC card (including memory card), or an optical card, or semiconductor memories such as a mask ROM, an ERPOM, an EEPROM, or a flash ROM.

In addition, it may be a structure in which the control devices 30, 30a, and 30b are connected to a communication network, and the program code is supplied through the communication network. The communication network is not particularly limited, and it is possible to use, for example, the Internet, an intranet, an extranet, a LAN, an ISDN, a VAN, a CATV communication network, a virtual private network, a telephone line network, a mobile communication network, a satellite communication network, or the like. In addition, a transmission medium which configures the communication network is not particularly limited, and it is possible to use, for example, a wire such as an IEEE 1394, a USB, a power line carrier, a cable TV line, a telephone line, or an ADSL line, or radio, for example, infrared light such as an IrDA, or a remote controller, the Bluetooth (registered trademark), 802.11 radio, an HDR (high data rate), a mobile phone network, a satellite line, or a terrestrial digital network. In addition, the present invention can be executed in a form of a computer data signal in which the program code is embodied through electronic transmission, and is embedded in a carrier wave.

The following configuration is also included in the present invention.

It is preferable that a storage unit which stores the optimal position which is specified by the specifying means be further included, and the optimal position which is stored in the storage unit be used when the fluorescence is detected.

According to the above configuration, it is not necessary to specify an optimal position each time fluorescence is detected. For this reason, an optimal position is specified once, a time required for specifying an optimal position is not needed thereafter.

Accordingly, it is possible to perform fast detecting processing of fluorescence.

It is preferable that a control mechanism which measures a distance between the light receiving unit and the test subject while making thereof be changed in a predetermined moving range be further included, and the distance be an index which denotes the relative position, and the specifying means specify the distance in which the light receiving intensity becomes a maximum as the optimal position from the moving range.

According to the above configuration, a relative position between the light receiving unit and the test subject is denoted using a distance between both. The "distance" also includes a case in which both are in contact with each other, and the light receiving unit is pushed by the test subject in addition to a case in which both are separated from each other. For example, a state in which both are in contact with each other may be set to a reference point (original point) of a distance in a case where both come closer from a state of being separated. In addition, it may be a case in which the distance becomes larger in the positive direction when both are further separated, and becomes larger in the negative direction when the light receiving unit is further embedded in the test subject after both came into contact.

By denoting a relative position between the light receiving unit and the test subject using a numerical value such as a distance, it is possible to make processing of specifying an optimal position easy by changing a relative position.

For this reason, it is possible to perform fast detecting processing of fluorescence.

It is preferable that a detection unit which detects a pressure that occurs between the light receiving unit and test subject, which changes with changes in a distance, be further included, and the specifying means specify the distance at which the light receiving intensity becomes a maximum using the pressure.

According to the above configuration, the distance is specified using a pressure which changes with the changes in distance (increasing and decreasing) without using a distance between the light receiving unit and the test subject. The "pressure" can be detected by, for example, interposing an elastic body and a pressure sensor between the light receiving unit and the test subject. It may be a structure in which the elastic body contracts when the light receiving unit is closer to the test subject, and as a result, a detected pressure increases. In this case, the reference point (original point; zero) of the pressure may be set to a state in which the light receiving unit and the test subject are farthest from each other.

By denoting a relative position between the light receiving unit and the test subject using a numerical value such as a pressure, it is possible to make processing of specifying an optimal position easy by changing a relative position.

For this reason, it is possible to perform fast detecting processing of fluorescence.

The light receiving unit is a unit which further receives reflected light as excitation light which is reflected from the test subject when the test subject radiates fluorescence, half-value width calculation means for calculating the half-value width of the reflected light is further included, the half-value width is an index which denotes the relative position, and it is preferable that the specifying means specify the half-value width of the reflected light of which the light receiving intensity of fluorescence becomes a maximum as the optimal position.

When a distance between the light receiving unit and the test subject, or a pressure therebetween is used, it is necessary to have a control mechanism for measuring those, accordingly a detection device may become large, or expensive that much.

According to the above configuration, it is preferable that reflected light be received together with fluorescence using the light receiving unit, and half-value width of the reflected light which is changed according to a change in a relative position between the light receiving unit and the test subject be calculated.

For this reason, it is possible to make a detection device simple, and inexpensive.

When the light receiving intensity calculation means is not able to calculated light receiving intensity of fluorescence which is received by the light receiving unit, it is preferable to further include informing means which informs of the fact.

According to the above configuration, when light receiving intensity cannot be calculated, informs a user the fact. A plurality of the informing contents are prepared in advance, and informing content thereof is selected according to an assumed situation in which light receiving intensity cannot be calculated. For example, when a peak value of light receiving intensity cannot be obtained, content such as "intensity of excitation light is extremely large, or extremely small" which is assumed to be the reason, may be informed.

For this reason, even when light receiving intensity cannot be calculated, a user understands the reason from the informed content, and is able to take an action corresponding to the situation.

An irradiation unit which irradiate a test subject with excitation light is further provided, and when the light receiving unit cannot calculate light receiving intensity of fluorescence which is received by the light receiving unit, it is preferable to further include adjusting means which adjusts at least one of an output intensity of excitation light which is irradiated by the irradiation unit and a relative position between the irradiation unit and the test subject so that the light receiving intensity of fluorescence which is received by the light receiving unit falls in an appropriate range of light receiving intensity which can be calculated by the light receiving intensity calculation means.

According to the above configuration, when light receiving intensity of fluorescence cannot be calculated, it is possible to calculate the light receiving intensity by settling the situation, by adjusting the light receiving intensity of excitation light, and a relative position between the irradiation unit and the test subject.

For example, when light receiving intensity of fluorescence cannot be calculated, there is a doubt that an output intensity of excitation light is extremely large. In this case, the adjusting means may adjust at least one of the output intensity of excitation light which is radiated by the irradiation unit and a relative position between the irradiation unit and the test subject in order to resolve the extremely large output intensity.

It is preferable that a display unit which displays an informing result of the informing means is further included.

According to the above configuration, a user is able to adjust the output intensity of excitation light, and a relative position between the irradiation unit and the test subject while viewing the informing result which is displayed on a display device, and to improve convenience of the user.

For example, when light receiving intensity of fluorescence cannot be calculated, there is a doubt that the output intensity of excitation light is extremely large. For this reason, the informing means informs of informing contents such as "Fluorescence is too strong. Please check the intensity of excitation light." In this case, a user is able to adjust at least one of the output intensity of excitation light which is radiated by the irradiation unit and a relative position between the irradiation unit and the test subject according to the message.

The detecting method according to the present invention is a detecting method in which fluorescence which is radiated from the test subject is detected in order to solve the above described problems, and the method includes a step of calculating a light receiving intensity which calculates a light receiving intensity of fluorescence which is received by the light receiving unit while changing a relative position between the light receiving unit which receives the fluorescence and the test subject; a step of specifying an optimal position of the relative position where the light receiving intensity of the fluorescence which is calculated in the step of calculating the light receiving intensity becomes a maximum; and a step of detecting the fluorescence using the optimal position which is specified in the step of specifying.

According to the above configuration, it is possible to exert the same effect as that in the detection device.

A step of manufacturing a fixing member for fixing the relative position to the optimal position is further included after the step of specifying, and it is preferable to make the relative position correspond to the optimal position using the fixing member in the step of detecting.

According to the above configuration, when the fixing member is manufactured once, it is possible to make a relative position between the light receiving unit and the test subject easily correspond to a specified optimal position using the fixing member.

In addition, the detection device may be realized using a computer, and in this case, since the computer is operated as the above described each means, a control program of the detection device which is realized using a computer, and a computer readable recording medium which is recorded with the program are also included in the category of the present invention.

INDUSTRIAL APPLICABILITY

The present invention can be applied to a detection device in which light receiving intensity of fluorescence becomes different when detecting the fluorescence, since a relative position between a test subject and a light receiving unit which receives fluorescence radiated from the test subject is different, and as a result, it is possible to detect fluorescence using an optimal position where the light receiving intensity becomes a maximum.

REFERENCE SIGNS LIST 1, 1a, 1b: DETECTION DEVICE
11: REFLECTION FIBER
12: INPUT FIBER
13: PROBE
13a: LIGHT RECEIVING UNIT, IRRADIATION UNIT
14: EXCITATION LIGHT SOURCE
15: DETECTOR
16, 16a: HOLDER
17: EXCITATION LIGHT SOURCE DRIVING CIRCUIT
18: STAGE CONTROL CIRCUIT (CONTROL MECHANISM)
19: STAGE (CONTROL MECHANISM)
21: SUPPORT FIXTURE
22: SETTING STAND
23: ELASTIC BODY (DETECTION UNIT)
24: PRESSURE SENSOR (DETECTION UNIT)
30, 30a, 30b: CONTROL DEVICE
31: SETTING UNIT (ADJUSTING MEANS)
32: LIGHT RECEIVING INTENSITY CALCULATION UNIT (LIGHT RECEIVING INTENSITY CALCULATION MEANS)
33, 33a: SPECIFYING UNIT (SPECIFYING MEANS)
34: INFORMING UNIT (INFORMING MEANS)
35: DISPLAY UNIT
36: STORAGE UNIT
37: HALF-VALUE WIDTH CALCULATION UNIT (HALF-VALUE WIDTH CALCULATION MEANS)
40: FIXING MEMBER
100: TEST SUBJECT

The invention claimed is:

1. A detection device which irradiates a test subject with excitation light, and detects fluorescence which is radiated from the test subject, the device comprising:
  a light receiving unit which receives the fluorescence;
  means for calculating a light receiving intensity of fluorescence which is received by the light receiving unit while changing a relative position between the light receiving unit and the test subject; and
  means for specifying an optimal position of the relative position where the light receiving intensity which is calculated by the means for calculating the light receiving intensity becomes a maximum, in which the fluorescence is detected using the optimal position which is specified by the means for specifying,
  wherein the light receiving unit further receives reflected light which is excitation light reflected from the test subject when the test subject radiates fluorescence,
  wherein means for calculating half-value width of the reflected light is further included,
  wherein the half-value width is an index denoting the relative position, and
  wherein the means for specifying specifies the half-value width of the reflected light of which light receiving intensity of the fluorescence becomes the maximum as the optimal position.

2. The detection device according to claim 1, further comprising:
  a storage unit which stores the optimal position which is specified by the means for specifying,
  wherein the optimal position which is stored in the storage unit is used when detecting the fluorescence.

3. The detection device according to claim 1, further comprising:
  means for informing which informs the fact when the means for calculating the light receiving intensity cannot calculate light receiving intensity of fluorescence which is received by the light receiving unit.

4. The detection device according to claim 3, further comprising:
a display unit which displays an informing result of the means for informing.

5. The detection device according to claim 1, further comprising:
an irradiation unit which irradiates the test subject with excitation light,
wherein, when the means for calculating the light receiving intensity cannot calculate light receiving intensity of fluorescence which is received by the light receiving unit, means for adjusting at least one of an output intensity of excitation light which is irradiated by the irradiation unit and a relative position between the irradiation unit and the test subject so that the light receiving intensity of fluorescence which is received by the light receiving unit falls in an appropriate range of light receiving intensity which can be calculated by the means for calculating the light receiving intensity.

6. A non-transitory computer readable recording medium on which a control program for causing a computer to function as each means of a detection device according to claim 1 is recorded.

7. A detecting method in which excitation light is radiated to a test subject, and fluorescence which is radiated from the test subject is detected, the method comprising:
a step of calculating a light receiving intensity of fluorescence which is received by the light receiving unit while changing a relative position between the light receiving unit which receives the fluorescence and the test subject;
a step of specifying an optimal position of the relative position where the light receiving intensity of fluorescence which is calculated in the step of calculating the light receiving intensity becomes a maximum; and
a step of detecting the fluorescence using the optimal position which is specified in the step of specifying,
wherein the light receiving unit further receives reflected light which is excitation light reflected from the test subject when the test subject radiates fluorescence, the method further comprising
calculating a half-value width of the reflected light,
wherein the half-value width is an index denoting the relative position, and
wherein the specifying step specifies the half-value width of the reflected light of which light receiving intensity of the fluorescence becomes the maximum as the optimal position.

8. The detecting method according to claim 7, further comprising:
a step of manufacturing a fixing member for fixing the relative position to the optimal position after the step of specifying,
wherein, in the step of detecting, the relative position is cause to correspond to the optimal position using the fixing member.

* * * * *